United States Patent
Kessler et al.

(10) Patent No.: US 8,465,497 B2
(45) Date of Patent: *Jun. 18, 2013

(54) TOOL FOR REMOVING OBJECT FROM THE BODY OF A PATIENT

(75) Inventors: Gerhard Kessler, Pfinztal (DE); Christian Gohlmann, Bruchsal-Untergrombach (DE); Rene Zusann, Worth (DE)

(73) Assignee: Angiomed GmbH & Co. Medizintechnik KG, Karlsruhe (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/346,480

(22) Filed: Jan. 9, 2012

(65) Prior Publication Data

US 2012/0103140 A1    May 3, 2012

Related U.S. Application Data

(63) Continuation of application No. 12/689,208, filed on Jan. 18, 2010, now Pat. No. 8,092,469, which is a continuation of application No. 10/312,275, filed as application No. PCT/EP01/06710 on Jun. 13, 2001, now Pat. No. 7,670,347.

(30) Foreign Application Priority Data

Jun. 20, 2000 (GB) .................................. 0015113.4

(51) Int. Cl.
*A61B 17/22* (2006.01)

(52) U.S. Cl.
USPC ........................................ 606/127; 604/96.01

(58) Field of Classification Search
USPC 606/114, 127, 128, 200; 604/96.01; 623/1.11
See application file for complete search history.

(56) References Cited

U.S. PATENT DOCUMENTS

| | | |
|---|---|---|
| 3,008,467 A | 11/1961 | Morris |
| 4,154,242 A | 5/1979 | Termanini |
| 4,611,594 A | 9/1986 | Grayhack et al. |
| 4,807,626 A | 2/1989 | McGirr |
| 5,193,533 A | 3/1993 | Body et al. |

(Continued)

FOREIGN PATENT DOCUMENTS

| | | |
|---|---|---|
| DE | 19722429 A1 | 12/1998 |
| EP | 0512729 A1 | 11/1992 |
| EP | 0737450 A1 | 10/1996 |
| EP | 0818180 A2 | 1/1998 |
| EP | 1292236 A1 | 3/2003 |

(Continued)

OTHER PUBLICATIONS

EP 01940570.3 filed Jun. 13, 2001 Office Action dated Dec. 22, 2005.

(Continued)

*Primary Examiner* — Victor Nguyen
(74) *Attorney, Agent, or Firm* — Rutan & Tucker, LLP

(57) ABSTRACT

A method for making a tool to remove a discrete object from the body of a human or animal patient includes a single length of Nitinol tubing and a sheath. The tubing includes a tool head section at a distal end of the tubing and a shaft section extending from a proximal end of the tubing to the tool head section. The tool head section includes a slitted section and a non-slitted section. The non-slitted section is disposed at a distal most end of the tubing. The slitted section includes a plurality of longitudinal slits forming a plurality of strands.

1 Claim, 3 Drawing Sheets

U.S. PATENT DOCUMENTS

| | | | |
|---|---|---|---|
| 5,496,330 A * | 3/1996 | Bates et al. | 606/127 |
| 5,792,145 A | 8/1998 | Bates et al. | |
| 5,795,322 A | 8/1998 | Boudewijn | |
| 5,810,874 A | 9/1998 | Lefebvre | |
| 6,443,972 B1 * | 9/2002 | Bosma et al. | 606/200 |
| 7,640,952 B2 | 1/2010 | Khachin et al. | |
| 7,670,347 B2 | 3/2010 | Kessler et al. | |
| 8,092,469 B2 | 1/2012 | Kessler et al. | |
| 2004/0026942 A1 | 2/2004 | Kessler et al. | |
| 2010/0121344 A1 | 5/2010 | Kessler et al. | |

FOREIGN PATENT DOCUMENTS

| | | |
|---|---|---|
| RU | 2022528 C1 | 11/1994 |
| WO | 9418888 A1 | 9/1994 |
| WO | 9623446 A1 | 8/1996 |
| WO | 9916365 A1 | 4/1999 |
| WO | 9948429 A1 | 9/1999 |

OTHER PUBLICATIONS

EP 01940570.3 filed Jun. 6, 2001 Response to Office Action dated Mar. 2, 2006.

ESCAPE Nitinol Retrieval Basket product brochure, Boston Scientific 2005.

PCT/EP2001/006710 filed on Jun. 13, 2001 International Preliminary Examination Report dated May 7, 2002.

PCT/EP2001/006710 filed on Jun. 13, 2001 Search Report dated Jul. 20, 2001.

U.S. Appl. No. 10/312,275, filed Jul. 31, 2003 Final Office Action dated Jan. 24, 2007.

U.S. Appl. No. 10/312,275, filed Jul. 31, 2003 Non-Final Office Action dated Aug. 24, 2006.

U.S. Appl. No. 10/312,275, filed Jul. 31, 2003 Non-Final Office Action dated Nov. 13, 2008.

U.S. Appl. No. 10/312,275, filed Jul. 31, 2003 Notice of Allowance dated Oct. 7, 2009.

U.S. Appl. No. 12/689,208, filed Jan. 18, 2010 Non-Final Office Action dated May 11, 2011.

U.S. Appl. No. 12/689,208, filed Jan. 18, 2010 Notice of Allowance dated Sep. 20, 2011.

* cited by examiner

TOOL FOR REMOVING OBJECT FROM THE BODY OF A PATIENT

PRIORITY

This application is a continuation of U.S. patent application Ser. No. 12/689,208, filed Jan. 18, 2010, now U.S. Pat. No. 8,092,469, which is a continuation of U.S. patent application Ser. No. 10/312,275, filed Jul. 31, 2003, now U.S. Pat. No. 7,670,347, which a U.S. national stage application under 35 USC §371 of International Application No. PCT/EP01/06710, filed Jun. 13, 2001, claiming priority to United Kingdom Patent Application No. 0015113.4, filed Jun. 20, 2000, each of which is incorporated by reference in its entirety into this application.

TECHNICAL FIELD

This invention relates to a tool which defines a basket cavity for removing a discrete object from the body of a human or animal patient, said tool having an elongate shaft having a tool head at a distal end thereof, said tool head having a radially compact disposition and a radially spread disposition for embracing said object.

BACKGROUND ART

The present applicant manufactures a device for catching, fixing and removing foreign objects form the body of a human patient. These foreign objects can include stones, fragments and concrements in the medical fields of urology and gastroenterology. In the present device, both ends of a number of individual wires are held together by a ring. Normally, the wires have a circular cross-section. One of these rings forms the distal end of a shaft and the other ring is spaced distally axially from the first ring. When the individual wires are all bowed radially outwardly and are distributed at regular intervals around the circumference of the axis, then these wires form longitudinal strands of an envelope defining a cavity centered on the long axis of the shaft. The wires are resilient and are given an outwardly bowed symmetrically or helically twisted shape so as to define a basket cavity radially inwardly of the envelope defined by the wires. The number of wires is usually in a range of from two to six. The entire device is placed within a sheath. For catching the foreign object, the distal end of the shaft and basket assembly is advanced out of the distal end of the sheath, allowing the resilience of the wires to form the basket by outward bowing. Once the foreign object is fished into the basket, then the shaft can be withdrawn proximally, to a greater or lesser extent, in order that the distal end of the sheath should squeeze down the diameter of the basket so that the basket wires grip the foreign object in the reduced diameter basket cavity immediately adjacent the distal end of the sleeve. Then the shaft and sleeve can together be withdrawn in the proximal direction to carry the foreign object in the basket out of the body.

In endoscopic surgery, a small diameter of the sheath is desirable. Currently the devices on the market have a sheath diameter falling within a range of outside diameters from 0.63 to 1.83 mm, which corresponds to a range of 1.9 to 5.5 French (1 French=⅓ mm).

One disadvantage of the presently marketed devices is that soldered, welded or glued joints are used to fix the individual wires to the rings and to the shaft. These connections represent a potential failure risk and, in any event, their ultimate strength has to be ascertained by extensive examination and testing.

Apart from this, the jointing of the wires at the rings defines the greatest outer diameter of the shaft element of the device, which therefore determines the inner diameter of the sheath and therefore indirectly determines the outer diameter of the sheath, setting a limit on the minimization of the outer sheath diameter.

Furthermore, the envelope of wires determines a characteristic mesh size of the basket and this mesh size has to be suitable both for fishing an object into the basket and then for retaining it within the basket until it has been removed from the body. Whereas a small mesh helps retention and removal, it does not help in the process of fishing the foreign object into the basket. A compromise mesh size has to be adopted.

EP-A-818 180 discloses an endoscope accessory in the form of a tube with a slitted distal end portion. The slits can be deformed radially outwardly to define a plurality of openings, by pulling from the proximal end of the tube on a pull wire 13 connected at its distal end to the distal end of the slitted portion. The disclosure of EP-A-737 450 is, in these respects, similar and U.S. Pat. No. 4,807,627.

EP-A-512 729 discloses an endoscopic surgical instrument which includes a tube having a slitted portion at its distal end. In a relaxed disposition of the wall portions between the slits, they are spaced apart from one another to form a basket. The slitted tube is itself co-axially within an outer tube having a distal end, and the basket can be closed down by drawing the basket, beginning at its proximal end, proximally into the outer tube, past the distal end of the outer tube. The slitted tube is made of a polyurethane material and the basket is formed by the application of steam heating to the slitted end.

DE-A-197 22 429 discloses a Nitinol tube, slitted at its distal end, for use as a basket to gather stones from bodily cavities. It is said to differ from previous such baskets in that the strands of the basket are unitary with the tube.

WO 94/18888 is another disclosure of a stone-gathering basket made from a plurality of Nitinol wires. The wires are arranged around the circumference of the basket in pairs and given a helical twist, which is said to increase the number of points of contact between the basket and entrapped calculi and to require of the physician no more dexterity than the prior art baskets, having a smaller number of contact points, required.

WO 96/23446 discloses a stone-gathering basket in which a distal half of the basket envelope exhibits a greater number of basket strands than the proximal half of the basket envelope. Each lengthwise strand in the proximal half of the baskets splits at half distance over the basket envelope into a plurality of strands which help to define the proximal half of the basket envelope. At the distal end of the basket is a cap to which all of the filaments defining the basket envelope are welded.

WO 99/16365 discloses a stone-gathering basket defined by a plurality of legs and with discussion what cross-sectional shapes of the legs are useful, and what surface topography on the inward facing surface of each leg.

WO 99/48429 is another disclosure of a stone gathering basket made unitary from a tube with longitudinal slits at its distal end, the basket being relaxed in its expanded configuration and of a material which can be a nickel titanium shape memory alloy such as Nitinol.

SUMMARY OF THE INVENTION

The present invention aims to mitigate some or all of the above-mentioned difficulties and, in any event, aims to improve present technology.

According to one aspect of the present invention, there is provided a medical device as described above, for removing a foreign object from the body of a human or an animal patient, which is characterized in that:

1. the shaft and tool head are formed from a single length of a tubing;
2. said tubing is slit lengthwise within a length contained within said tool head and stopping short of a distal end surface of said tube, thereby to form at least three parallel first strands which together define an envelope of said basket cavity; and.
3. the tool is provided with a set of second strands, each formed by slitting one of the first strands over a distal portion of said first strand, which distal portion is less than the full length of the first strand.

In this way, it can be arranged that the mesh size of the basket structure, of the distal end of the basket, is provided as smaller apertures than are present at the proximal end of the basket. In this way, foreign objects can be fished into the basket at its proximal end, after which they can be retained in the smaller aperture mesh at the distal end of the basket. In one preferred embodiment, the second strands have a length in a range of from 45% to 80% of the length of the first strands.

It will be appreciated that, in the tool of the present invention, no joints are required. The basket is instead made from the base tubing of the shaft of the tool.

Further, it will be appreciated that the largest diameter of the tool is represented by the basic tubing itself, there being no larger diameter of rings at each end of the basket.

Conceivably, a basket could be constructed by slitting each of the second strands over a portion of its length which is less than the full length of the second strand, thereby to define a set of third strands over part of the length of the basket, setting a aperture size in that zone of the length of the basket smaller than would otherwise be the case in the absence of the third strands. For example, the zone of the third strands could be in a "belly portion" of the basket where its diameter is close to its maximum, thereby to achieve an aperture size in this belly portion smaller than an aperture size in a proximal half of the basket envelope, thereby better to retain an object captured in the proximal half of the basket in the smaller mesh size of the distal half of the basket.

Conveniently, the tubing is made from nickel titanium shape memory alloy and the strands are formed by a narrow diameter laser beam which cuts through the wall of the tubing.

It will be appreciated that, the device being based on a tube, there is the possibility to provide a guide wire or other core wire during use of the tool. For example, one could advance the tool into position along a previously placed guide wire. For laser cutting, one could set within the tubing work piece a core, so that the incident laser beam passes through one wall thickness and into the core, but not beyond the core into the wall thickness of the tubing on the opposite side of the core. In this way, one could slit the tube at 120° intervals around its circumference in order to create three first strands, and then the laser could be used to slit each of the three first strands, along a distal portion of its length, into two second strands, making a total of six second strands distributed at sixty degree intervals around the circumference of the tubing.

BRIEF DESCRIPTION OF THE DRAWINGS

For better understanding of the present invention, and to show more clearly how the same are recurred into effect, reference will now be made, by way of example, to the accompanying drawings, in which.

DETAILED DESCRIPTION

Figure 1:
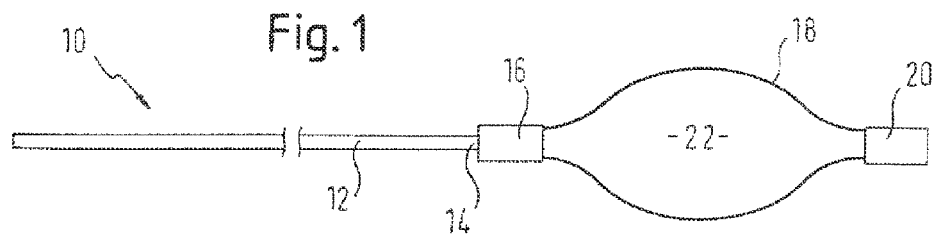
FIG. 1 is a longitudinal diagrammatic section of a prior art tool for removing a foreign object from the body of a patient.

Referring to FIG. 1, a conventional tool has a shaft 12 with a distal end 14 on which is mounted a first ring 16. Welded within the open distal end of the ring 16, side by side, are four nickel titanium shape memory alloys circular section wires 18. All four distal ends of the wire 18 are welded within an end ring 20 spaced from the distal end 14 to the shaft 12 and itself representing a distal end of the device 10. Each of the wires 18 is given a bowed shape, as shown in the figure, by thermal treatment as is understood by those skilled in this art. The entire device is telescoped within a sleeve (not shown) having an inner diameter big enough to accommodate the rings 16 and 20.

For catching and removing foreign objects, the distal end of the sleeve is advanced to a desired location within the body and then the shaft 12 is advanced until the basket 18 opens just distally beyond the distal end of the sleeve. Moving the sleeve, the medical practitioner fishes the target object into the cavity 22 within the basket defined by the wires 18, and the shaft 12 is withdrawn proximally by a distance sufficient for the distal end of the sheath to squeeze the wires 18 onto the foreign object, thereby retaining it within the basket cavity 20. Then the sheath and shaft are together withdrawn proximally, carrying the object out of the body.

The method of use of a tool in accordance with the present invention is similar. However, the manufacture of the tool is quite different, as can be seen from FIG. 2.

Figure 2:
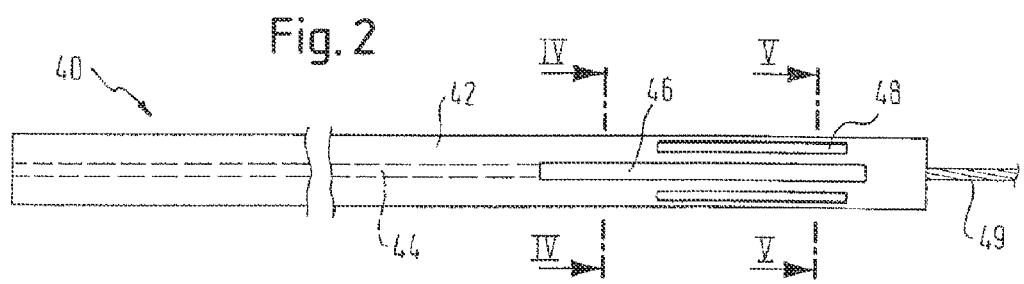
FIG. 2 is a similar section through a first embodiment of a tool in accordance with the present invention, in its compact disposition.

FIG. 2 shows a tool 40 based on a single length of tubing 42 having a lumen 44 which runs its full length. The tube is of Nitinol shape memory alloy. Near the distal end of the tube 42 is provided a plurality of slits, comprising a set of four first slits 46 arranged at ninety degree intervals around the circumference of the tube 42. Evenly spaced between each pair of first slits 46 are the slits of a set of four second slits 48, again made by laser. FIG. 2 shows a core wire 49 which can be placed within the lumen 44, at the distal zone of the tubing 42, if it is desired for the incident laser beam to penetrate only one wall thickness of the tubing 42, and not go beyond the lumen 44 (as would be appropriate if, for example, an arrangement of three first slits 46, at 120 degree intervals around the circumference of the tubing 42, were to be specified). The length of the set of first slits 46 corresponds to the desired length of the object-catching basket of the tool 40.

Figure 3:
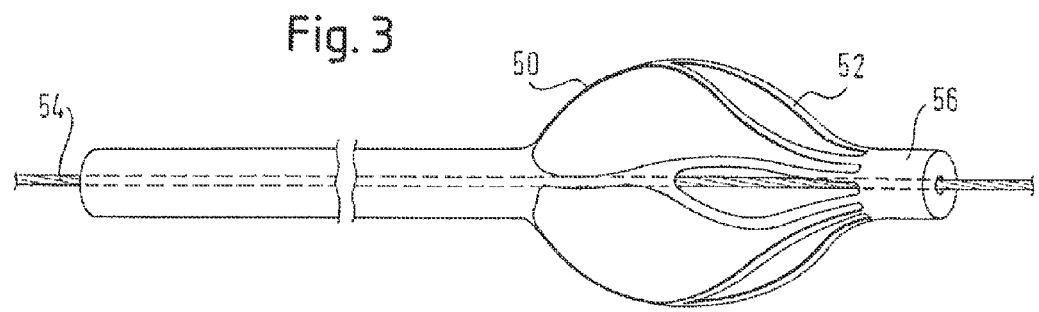
FIG. 3 is a section corresponding to FIG. 2, and showing the FIG. 2 tool in spread disposition.

Now referring to FIG. 3, the basket of the FIG. 2 tool can be seen in its spread disposition. Just as Nitinol stents are given a remembered dimension by heat treatment, so the tool of FIG. 2 is given by heat treatment the basket shape illustrated in FIG. 3. Thus, when the tubing 42 is advanced into a surrounding sheath, the strands 50 between adjacent first slits 46, and the strands 52, between adjacent first and second slits 46, 48, are squeezed down from the spread disposition of FIG. 3 into the compact disposition shown in FIG. 2. Then, when the distal end of the tubing 42 is advanced distally out of the distal end of the sleeve, the strands 50 and 52 can take up the remembered deployed disposition of FIG. 3.

Figure 4:
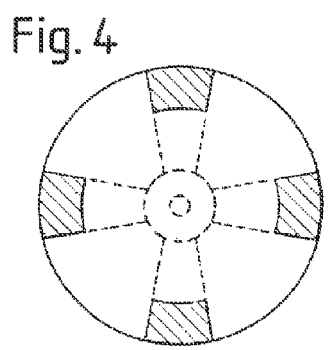
FIG. 4 shows a transverse section through line IV-IV in FIG. 2.
Figure 5:
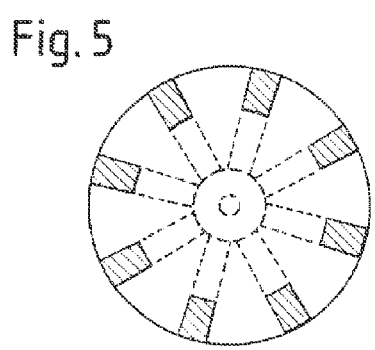
FIG. 5 is a transverse section through line V-V of FIG. 2.

FIGS. 3, 4 and 5 reveal a valuable technical effect of the present invention, namely, that the mesh size of the basket can be varied, from one end of the basket to the other, allowing foreign objects to be introduced into the basket envelope through the relatively wide aperture zone of the proximal end of the basket, but then more securely retained within the basket at the relatively smaller diameter aperture portions at the distal end of the basket. Note also in FIG. 3 the presence of a guide wire 54. The tool could be advanced on such a guide wire, into a desired location, then the guide wire 54 could be withdrawn proximally, to leave the basket cavity empty, and then the foreign object could be fished into the basket.

Figure 6:
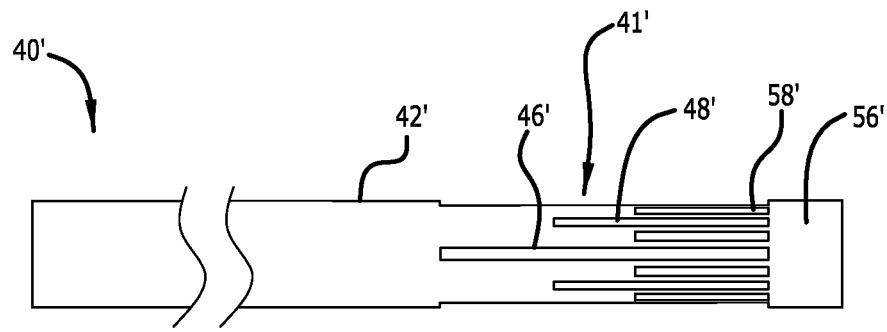
FIG. 6 is a longitudinal diagrammatic section of another embodiment of a tool in accordance with the present invention, in its compact disposition.

FIG. 6 shows a tool 40' based on a single length of tubing 42' having a lumen 44' that runs its full length. Near the distal end of the tube 42' is provided a slitted section 41' and a non-slitted section 56' having a length less than a length of slitted section 41'. The slitted section 41' includes a plurality of slits, comprising a set of four first slits 46' arranged at ninety degree intervals around the circumference of the tube 42'. At a distal end of the first slits 46' and evenly spaced between each pair of first slits 46' are the slits of a set of four second slits 48', again made by laser. At a distal end of the second slits 48' and evenly spaced between each pair of second slits 48' are the slits of a set of eight third slits 58', again made by laser. Other slit arrangements are contemplated, such as, for example, three first slits 46' at 120 degree intervals around the circumference of the tubing 42'. The length of the set of first slits 46' corresponds to the desired length of the object-catching basket of the tool 40'.

Figure 7:
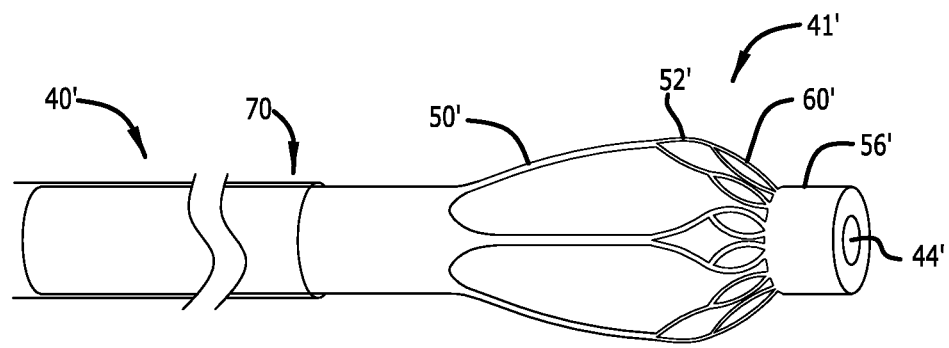
FIG. 7 is a section corresponding to FIG. 6, and showing the FIG. 6 tool in spread disposition.

Referring to FIG. 7, the basket of the FIG. 6 tool can be seen in its spread disposition following distal advancement of the tubing 42' out of the distal end of the sleeve 70. The basket may be constructed by slitting each of the first strands 50' over a distal portion of its length, which is less than the full length of the first strand, thereby defining a set of second strands 52'. These second strands 52' may be further slit over a distal portion of its length which is less than the full length of the second strand, thereby defining a set of third strands 60' over a distal part of the length of the basket, setting an aperture size in that zone of the length of the basket smaller than would otherwise be the case in the absence of the third strands 60'. The resulting strands achieve an aperture size smaller at the distal end than at the proximal end of the basket envelope, thereby better to retain an object in the smaller mesh size of the distal half of the basket, yet captured in the larger mesh size of the proximal half of the basket.

Figure 8:
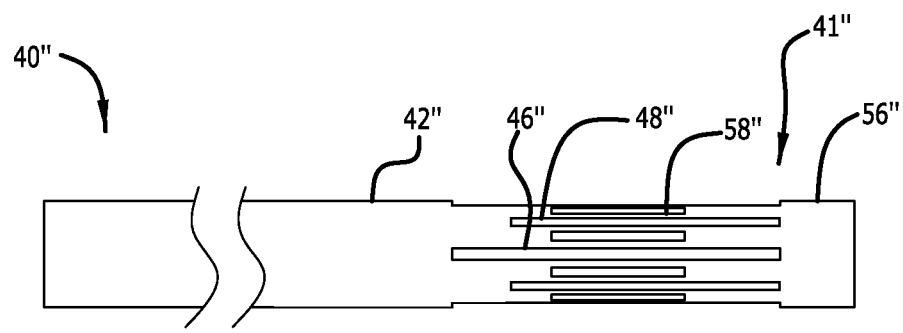
FIG. 8 is a longitudinal diagrammatic section of yet another embodiment of a tool in accordance with the present invention, in its compact disposition.

FIG. 8 shows a tool 40" based on a single length of tubing 42" having a lumen 44" which runs its full length. Near the distal end of the tube 42" is provided a slitted section 41" and a non-slitted section 56" having a length less than a length of slitted section 41". The slitted section 41" includes a plurality of slits, comprising a set of four first slits 46" arranged at ninety degree intervals around the circumference of the tube 42". Evenly spaced between each pair of first slits 46" are the slits of a set of four second slits 48", again made by laser. Evenly spaced between each pair of second slits 48" are the slits of a set of eight third slits 58", again made by laser. Other slit arrangements are contemplated, such as, for example, three first slits 46" at 120 degree intervals around the circumference of the tubing 42". The length of the set of first slits 46" corresponds to the desired length of the object-catching basket of the tool 40".

Figure 9:
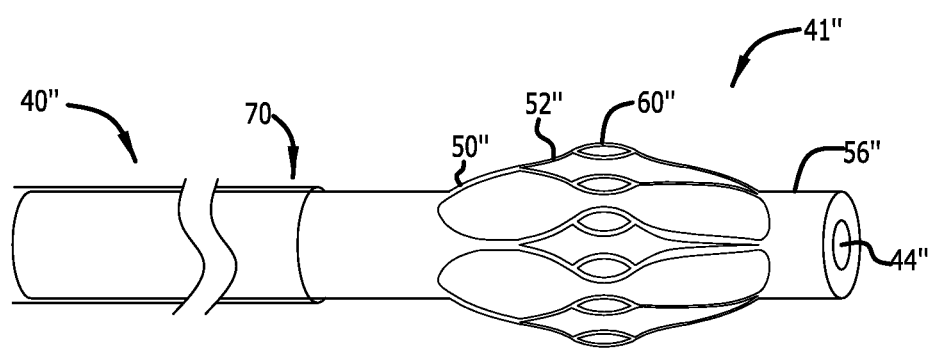
FIG. 9 is a section corresponding to FIG. 8, and showing the FIG. 8 tool in spread disposition.

Referring to FIG. 9, the basket of the FIG. 8 tool can be seen in its spread disposition following distal advancement of the tubing 42" out of the distal end of the sleeve 70. In this embodiment, the first strands 50" extend along the a distal region of the tool head, stopping short of a distal end surface of the tubing. Second strands 52" are within a distal portion of the first strand 50", where the length of the second strand 52" is less than a length of the first strand 50". In a spread disposition, the second strand 52" extends from a side of the first strand 50" and is directed distally along its length toward the distal end of the tubing 42". Third strand 60" is within a portion of the second strand 52", where the length of the third strand 60" is less than the length of the second strand 52". In the spread disposition, the third strand 60" extends from a side of the second strand 52" and is directed distally along its length toward the distal end of the tubing 42". The distalmost ends of the first strands 50" and second strands 52" may be secured together at the tip 56". In one embodiment, the zone of the third strands could be in a "belly portion" of the basket where its diameter is close to its maximum, thereby to achieve an aperture size in this belly portion smaller than an aperture size in a proximal half of the basket envelope, thereby better to retain an object captured in the proximal half of the basket in the smaller mesh size of the distal half of the basket.

Not immediately evident from the drawings is a further useful technical effect of the present invention. Whereas the distal ring 20 of the prior art device has a relatively significant length, the unslitted distal tip 56 of a device in accordance with present invention could be made relatively much shorter in length. This could improve the performance of the device when it is desired to fish into the basket an object which lies rather close to a tissue wall surface within a cavity or lumen of a body.

The cutting by laser of slits within the cylindrical wall surface of a tube of Nitinol shape memory alloy is a technology which is by now relatively well understood by those companies which specialize in the manufacture of self-expanding stents. For such companies, it will be apparent from the above description that the accompanying drawings and specific description given above represents only one example of how the concept of the present invention can be realized. The concept of the invention permits a new combination of stone destruction in situ by lithotripsy. The technique of lithotripsy involves hitting a stone with a probe which is itself struck by a projectile at the proximal end of the lithotripsy probe, to provide a kinetic energy ballistic impact on the stone to fragment the stone. It is envisaged that the device of the present invention would trap the stone and then a lithotripsy probe would be introduced into the proximal end of the tubular shaft and advanced into the basket at the distal end, to attack the stone trapped therein. A suitable probe can be obtained from EMS Electromedical Systems SA, CH-1347, Le Sentier, Switzerland.

To such readers, variations and modifications of these specific description above will be evident. The scope of the claims which follow is not to be taken as limited to the specific details of the description given above.

The invention claimed is:

1. A method for making a tool to remove a discrete object from the body of a human or animal patient, comprising:

providing a single Nitinol tubing having a proximal end and a distal end;

forming a tool head section by slitting the distal end of the tubing, the tool head section distinct from a shaft section extending proximally from the tool head section to the proximal end of the tubing, the tool head section having a first length and the shaft section having a second length greater than the first length, the forming comprising slitting the tool head section to form a slitted section having a third length and a non-slitted section having a fourth length less than the third length, the non-slitted section disposed at a distal most end of the tool head section, the slitted section including four longitudinal slits forming four strands separated from one another by about 90 degrees; and surrounding the tubing with a sheath, the slitted section translating from a compact disposition within the sheath to an expanded spread position when advanced distally out of a distal end of the sheath.

\* \* \* \* \*